(12) United States Patent
Litzler et al.

(10) Patent No.: US 8,545,261 B2
(45) Date of Patent: Oct. 1, 2013

(54) ELECTRICAL CONNECTION SYSTEM BETWEEN AN ELECTRICAL IMPLANTED MEDICAL DEVICE

(75) Inventors: Pierre-Yves Litzler, Saint Martin du Vivier (FR); Pierre Sabin, Paris (FR)

(73) Assignee: Centre Hospitalier Universitaire de Rouen, Rouen (FR)

( * ) Notice: Subject to any disclaimer, the term of this patent is extended or adjusted under 35 U.S.C. 154(b) by 35 days.

(21) Appl. No.: 13/262,917

(22) PCT Filed: Apr. 23, 2010

(86) PCT No.: PCT/EP2010/055425
§ 371 (c)(1),
(2), (4) Date: Oct. 4, 2011

(87) PCT Pub. No.: WO2010/122139
PCT Pub. Date: Oct. 28, 2010

(65) Prior Publication Data
US 2012/0028490 A1    Feb. 2, 2012

(30) Foreign Application Priority Data
Apr. 23, 2009  (FR) ...................................... 0952657

(51) Int. Cl.
*H01R 11/00*    (2006.01)
(52) U.S. Cl.
USPC ........................................ 439/502; 439/439
(58) Field of Classification Search
USPC ........... 439/439, 502, 796, 864, 909; 607/36, 607/37
See application file for complete search history.

(56) References Cited

U.S. PATENT DOCUMENTS

| 4,411,276 A | 10/1983 | Dickhudt et al. |
| RE32,947 E | 6/1989 | Dormer et al. |
| 4,934,366 A | 6/1990 | Truex et al. |

(Continued)

FOREIGN PATENT DOCUMENTS

| DE | 8617583 | 8/1986 |
| EP | 0 280 301 | 8/1988 |

(Continued)

OTHER PUBLICATIONS

P. Sabin et al., Permanent percutaneous electrical connection. General principals. Rev Laryngol Otol Rhinol. 1997, pp. 335-342.

(Continued)

*Primary Examiner* — Thanh Tam Le
(74) *Attorney, Agent, or Firm* — Blakely Sokoloff Taylor & Zafman

(57) ABSTRACT

An electrical connection system to electrically connect an internal electrical device (2) positioned inside an animal's body with an external electrical device (3) positioned outside the animal's body. The system includes a cable (4) positioned at least partially inside the animal's body and enclosing at least one electrical wire. The cable (4) has at one end a first connector (5) to connect the at least one electrical wire with an external electrical device (3). The cable (4) has at its other end a second connector (1) placed inside the animal's body. The second connector (1) has connectors to allow an electrical connection between the at least one cable (4) and the internal electrical device (2). The second connector (1) includes additional connectors to allow a removable electrical connection between at least one electrical wire external to the cable (4) and the internal electrical device (2).

11 Claims, 2 Drawing Sheets

(56) References Cited

U.S. PATENT DOCUMENTS

| | | | |
|---|---|---|---|
| 4,941,472 | A | 7/1990 | Moden et al. |
| 4,954,105 | A | 9/1990 | Fischer |
| 5,095,903 | A | 3/1992 | DeBellis |
| 5,855,494 | A * | 1/1999 | Blaszczyk et al. ............ 439/502 |
| 5,919,213 | A | 7/1999 | Nelson et al. |
| 6,043,273 | A | 3/2000 | Duhaylongsod |
| 6,070,103 | A | 5/2000 | Ogden |
| 6,280,243 | B1 * | 8/2001 | Liu et al. ....................... 439/502 |
| 6,540,549 | B2 * | 4/2003 | Rupert ........................... 439/502 |
| 6,790,077 | B1 * | 9/2004 | Chen .............................. 439/502 |
| 7,004,787 | B2 * | 2/2006 | Milan ............................ 439/502 |
| 7,252,542 | B2 * | 8/2007 | Chen .............................. 439/502 |
| 7,488,187 | B2 * | 2/2009 | Wolf .............................. 439/106 |
| 7,494,370 | B2 * | 2/2009 | Chang et al. .................. 439/502 |
| 7,803,021 | B1 * | 9/2010 | Brase ............................. 439/668 |
| 8,079,846 | B1 * | 12/2011 | Cookson ......................... 439/13 |
| 8,109,792 | B2 * | 2/2012 | Briano et al. ............ 439/620.21 |
| 8,233,986 | B2 * | 7/2012 | Deininger et al. ............... 607/37 |
| 2008/0208267 | A1 | 8/2008 | Alexander et al. |

FOREIGN PATENT DOCUMENTS

| | | |
|---|---|---|
| EP | 1 504 789 | 7/2005 |
| FR | 2568477 | 2/1986 |
| FR | 2 832 778 | 5/2003 |
| WO | WO 92/22107 | 12/1992 |
| WO | WO 98/57702 | 12/1998 |
| WO | WO 99/46002 | 9/1999 |
| WO | WO 03/092794 | 11/2003 |

OTHER PUBLICATIONS

P. Sabin et al., A new application for extra-oral implants: the permanent percutaneous electrical connection, 1999, pp. 123-131, Masson, Paris.

* cited by examiner

ELECTRICAL CONNECTION SYSTEM BETWEEN AN ELECTRICAL IMPLANTED MEDICAL DEVICE

This is a non-provisional application claiming the benefit of International application number PCT/EP2010/055425 filed Apr. 23, 2010.

FIELD OF THE INVENTION

The present invention concerns electrical connections in the medical field, and more particularly an electrical connection system between a power supply device and a medical device implanted in the body of an animal, in particular in the human body.

TECHNICAL BACKGROUND

There have been major advances in electrical equipment designed to be installed inside a patient's body within the past few years. We can cite, as non-limiting examples, medical devices implanted to compensate for failure of a natural organ, such as the heart, for example, devices that monitor certain physiological parameters, or even devices suitable to deliver a particular dose of a particular therapeutic substance at a given time and in a specific part of the body.

A recurrent problem for all these implanted medical devices resides in managing the power supply that allows them to operate in a lasting manner. Although some of these implanted medical devices can work on a battery due to their low energy consumption, the majority of implanted medical devices consume a great deal of energy, which necessitates an ongoing power supply, most often using a power source external to the patient.

Thus, such types of implanted medical devices are often connected to an external power supply device by means of a percutaneous electrical cable. Although this electrical connection means is simple to implement during the surgical procedure, and often used for implanting medical devices temporarily, it has many risks of infection at the percutaneous passage of the connection cable.

Now, if an infection of the percutaneous passage spreads along the connection cable to the corresponding implanted medical device, it may cause a malfunction or even total breakdown of the implanted medical device.

Consequently, when an infection is detected at the percutaneous passage for the connection cable, it is necessary to change the connection cable before the infection neutralizes the implanted medical device.

For implanted electrical devices whose interrupted operation would not be life-threatening for the patient, changing the connection cable can be done simply by disconnecting the infected cable and replacing it with a sterile cable, or even by replacing the entire device if replacement of the cable alone is not possible.

However, for some other implanted medical devices, this is not the case, and interrupting their power supply risks, if the device concerns a vital role in the patient's survival, causing severe discomfort or even death of the patient. This is the case, for example, for heart pumps such as implanted left ventricular assist devices (LVAD) for which interrupting operation for the several minutes required to replace the cable would be fatal to the patient, especially a patient with terminal heart failure. In this case, it is therefore not possible to stop the progression of the infection by changing the connection cable.

A goal of the present invention is to provide an electrical connection system to electrically connect a medical device designed to be positioned inside an animal's body with a power supply device intended to be positioned outside the animal's body that allows resolving the problems outlined above in connection with infections that could neutralize the medical device.

In particular, a goal of the present invention is to provide an electrical connection system that allows maintaining the power supply of the implanted medical device during the replacement of infected elements to stop the progression of the infection up to the medical device.

Another goal of the present invention is to provide assemblies made up of a medical device designed to be implanted in the body of an animal, such as a human, and for which the risks of malfunction or breakdown due to infections could be treated while reducing, or even eliminating, the risks for the patient.

DISCLOSURE OF THE INVENTION

For this purpose, we propose an electrical connection system to electrically connect an internal electrical device designed to be positioned inside the body of an animal with an external electrical device designed to be positioned outside the animal's body, said system including a cable intended to be positioned at least partially inside the animal's body and enclosing at least one electrical wire, said cable having a first connection means at one of its ends to connect said cable to at least one electrical wire of the external electrical device, characterized in that the cable further includes at its other end a second connection means intended to be positioned inside the animal's body, the second connection means having connectors to permit an electrical connection between said at least one electric wire of the cable and the internal electrical device, the second connection means further having additional connectors to allow an electrical connection between at least one electrical wire external to said cable and the internal electric device.

Some preferred but non-limiting aspects of this electrical connection system, taken alone or in combination, are the following:
- the system further includes a second cable intended to be positioned at least partially inside the animal's body and enclosing at least one electric wire, said second cable having at one of its ends a third connection means to connect said at least one electrical wire of the second cable with an external electrical device, said at least one electrical wire of the second cable being further connected to at least one of the additional connectors of the second connection means, in order to connect the second cable to the internal electrical device.
- the third connection means of the second cable is a subcutaneous electrical connector.
- the third connection means of the second cable is an electrical connector in the form of a percutaneous socket.
- the first connection means of the first cable is an electrical connector in the form of a percutaneous socket.
- the second connection means has connectors allowing a removable connection of electrical wires.
- the connectors of the second connection means have components for compressing electrical wires, said compression components having the form of rotatably-mounted cams designed to be engaged against these electrical wires.

the connectors of the second connection means further comprise locking components that allow locking the rotation of the compression components in order to hold them in position.

the second connection means has an activation means to activate the electrical connection between said at least one electrical wire of the cable and the internal electrical device, and/or to activate the electrical connection between said at least one electrical wire external to said cable and the internal electrical device.

According to another aspect of the invention, a cardiac assist assembly is proposed, characterized in that it comprises:

an internal electrical device in the form of a heart assist pump designed to be implanted in an animal while replacing all or part of the animal's heart;

a connection system such as previously described removably connected to the heart assist pump by means of the connectors of the second connection means.

According to a preferred but non-limiting aspect of this heart assist assembly, the first connection means of the connection system is designed to be positioned outside the animal's body.

According to another aspect of the invention, we propose an assembly for delivering a therapeutic substance to the inside of an animal's body, characterized in that it comprises:

an internal electrical device in the form of a device for releasing a therapeutic substance designed to be implanted in an animal to allow delivering said therapeutic substance in specific areas for treating the animal;

a connection system such as previously described removably connected to the device for releasing a therapeutic substance by means of the connectors of the second connection means.

According to another aspect of the invention, we propose a power generation assembly, characterized in that it comprises:

an internal electrical device containing an internal power supply device designed to be implanted in an animal and having means for being electrically connected to at least one medical device designed to be implanted in said animal;

a connection system such as previously described removably connected to the internal power supply device by means of the connectors of the second connection means.

DESCRIPTION OF THE FIGURES

Other characteristics and advantages of the invention will appear from the following description, which is purely illustrative and non-limiting and should be read with regard to the attached drawings, in which.

DETAILED DESCRIPTION OF THE INVENTION

As seen above, there are more and more implanted medical devices requiring continuous power supply by means of an electrical connection cable, acting as a power cable, positioned percutaneously and therefore having the disadvantage that it can become infected at the percutaneous passage and that this infection can spread to the implanted medical device, which one is seeking to avoid.

In addition to the fact that there are a certain number of medical devices for which it is impossible to stop operation for a sufficiently long time to be able to replace the infected power supply cable without putting the patient's life in danger, there are also a certain number of cases where the power supply cable cannot be replaced independently of the medical device. In these cases, it is necessary, if we wish to stop the progress of the infection, to replace the entire medical assembly made up of the implanted medical device and the percutaneous power cable, which represents very high costs, both with regard to the equipment to be replaced and to the surgical procedure itself.

In order to resolve this issue, we propose a novel electrical connection system that has the feature of being removable with regard to the implanted medical device, while having a back-up power supply parallel to the main power supply; this back-up power supply allows supplying the implanted medical device when the main power supply cable of the connection system that is infected must be removed to be replaced.

Figure 1:
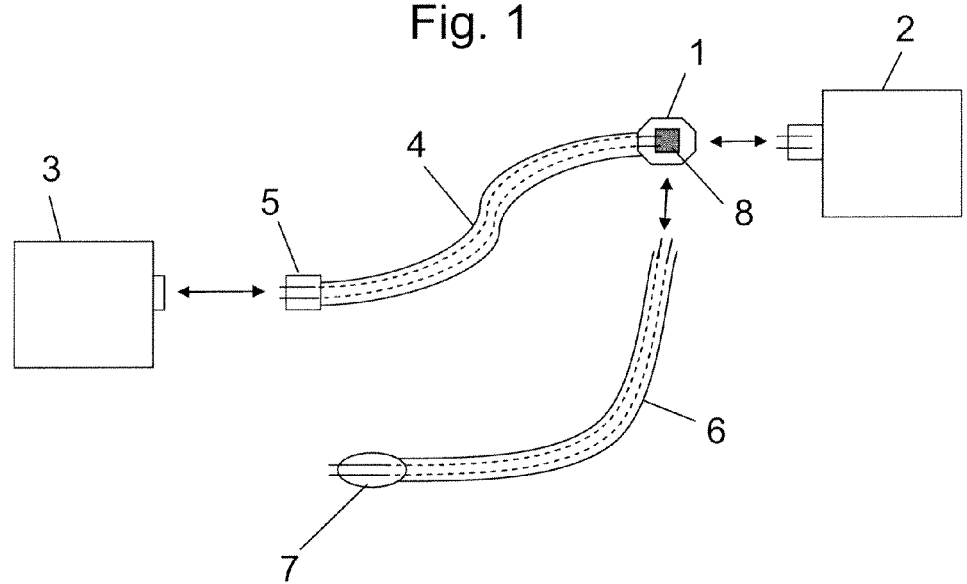
FIG. 1 is a schematic representation of the electrical connection system proposed.

As is shown schematically in FIG. 1, the electrical connection system proposed comprises a main power supply cable 4 with a certain number of electric wires that allow passing an electrical current between a power supply device 3 external to the human body and electrical medical device 2 implanted in the patient's body. This main power cable 4 preferably has the same characteristics as the conventional power supply cable; in particular, main power supply cable 4 is designed to be positioned percutaneously to electrically connect external power supply system 3 to implanted medical device 2.

The special feature of this proposed electrical connection system resides in the electrical connection between main supply cable 4 and implanted medical device 2.

Indeed, the end of the main power cable 4 designed to be connected to electrical implanted medical device 2 comprises a particular connection device 1, which is designed, on the one hand, to allow an electrical connection between the wires of the same electrical phase of main power supply cable 4 and electrical implanted medical device 2, this connection being done by means of particular connectors and interconnection means, and which further includes additional connectors arranged to allow an electrical connection between the electrical wires of implanted medical device 2 and electrical wires external to main power cable 4.

Connection device 1 positioned at the implanted end of main power supply cable 4, and for which we will show a particular embodiment later on in this text, thus allows connecting a second assembly of electrical wires, assembled, for example, in a secondary electrical cable 6, to implanted medical device 2. In particular, the electrical connection system proposed therefore permits having a second power supply in parallel to the first power supply so as to be able to supply power to implanted medical device 2 by this second power supply if this proves necessary.

Let's take the non-limiting example of the case where the implanted medical device is an implanted left ventricular assist device (LVAD) heart pump, for which continuous power supply is usually provided by means of an electrical cable fixed in a non-removable manner to the pump, and coupled percutaneously to a power source outside the patient.

Such heart assist pumps are generally implanted temporarily in the patient, but implantation durations are becoming increasingly longer today, so that it is not rare for the power supply cable to break or become infected from the corresponding percutaneous passage. As soon as the infection begins at the percutaneous passage, the infection spreads along the power cable in the direction of the heart assist pump, and it is therefore vital to be able to stop this spread of the infection before it reaches the pump in order to save the patient's life.

By using a heart assist pump associated with a power supply system in the form of the electrical connection system proposed, it is possible to stop the spread of the infection by replacing the main power supply cable in a relatively simple and inexpensive way.

In fact, in this case, electrical implanted medical device 2, i.e., the heart assist pump, is connected to a main power supply cable 4 by means of a particular electrical connection device 1 that allows connecting a second power supply cable 6 parallel to main power supply cable 4. Thus, when main power supply cable 4 is infected, it is possible to connect a second power supply source to the implanted electrical medical device by means of a second power supply cable 6 connected to electrical connection device 1. With such a connection system, it is therefore possible to cut the main power supply while continuing to provide the heart assist pump with power by means of second power supply cable 6 coupled to an energy source, thus guaranteeing the continuous operation of the pump.

As soon as the heart assist pump is supplied by a secondary power source, it is possible to disconnect main power cable 4 from connection device 1 so as to remove it from the patient and eliminate any source of infection. Main power supply cable 4 can therefore be replaced easily without putting the patient's life in danger by stopping an implanted medical device since this device continues to be supplied by means of second power supply cable 6 connected to electrical connection device 1. Once infected main power supply cable 4 is removed, a new one can be inserted under sterile conditions, to connect to electrical connection device 1 on one side and to external power supply source 3 on the other side, so that the heart assist pump can again be supplied with power by means of main power supply cable 4. In this case, emergency power supply cable 6, positioned for purposes of the procedure, can be removed, and the percutaneous passage for main electrical supply cable 4 reclosed so as to return implanted electrical medical device 2 to standard operation by means of main power supply cable 4 connected to external power supply source 3.

In order to be conducted under optimal conditions for success, the change of main power supply cable 4 requires a rigorous surgical protocol meeting several requirements:

first, connect emergency power supply cable 6 under sterile conditions, by making a first antiseptic surgical approach opposite connection device 1 coupled to electrical implanted medical device 2;

second, remove infected main power supply cable 4 by disconnecting it from connection device 1, and by pulling it to the outside of the body while avoiding spreading the infection that one seeks to eradicate.

Therefore, it is necessary to perform a surgical procedure requiring very rigorous antisepsis near an area infected by bacteria that are not exceptionally resistant to current antibiotics.

According to another embodiment of the invention, the proposed electrical connection system is implanted, connected on one side to implanted medical device 2 and on the other side to external power supply device 3, by means of main power cable 4 connected to proposed connection device 1, the connection system further comprising an emergency power cable 6 whose electrical wires are connected to additional connectors of connection device 1 so as to be interconnected with the electrical wires of the same phase of the electrical implanted medical device 2.

In this case, emergency power supply cable 6 is connected at one of its ends to connection device 1, and is connected at its other end to specific connection means 7 by means of which it is possible to connect said emergency power supply cable 6 to a power source outside the patient.

This assembly composed of emergency power supply cable 6, by means of additional electrical connections 7, combined with connection device 1 presented, constitutes an additional emergency electrical connection (AEEC).

Additional electrical connection means 7 positioned at the free end of emergency power supply cable 6 can have different forms. Preferably, connection means are used that are designed to be positioned subcutaneously so as to be easily accessible by a practitioner from outside the patient without necessarily having to make specific incisions.

For example, a socket positioned subcutaneously and comprising connectors in the form of female sockets can be used, in which it is possible to implant pins connected to an external power supply source, and by means of which electricity can be conducted to emergency power supply cable 6.

Preferably, these subcutaneous connection means 7 are arranged and positioned in the patient so as to be easily and reliably accessible from the outside.

Subcutaneous connector 7 may, for example, have the form of an open housing having several internal compartments insulated electrically from one another, each compartment being filled with a conductive material into which the electrical connection plugs can be inserted. The conductive material of each compartment is further connected to the electrical wires of emergency power supply cable 6. Furthermore, a sealing membrane seals the housing, said sealing membrane being formed of an insulating and flexible material designed for insertion of electrical connection plugs from outside the housing through said sealing membrane to the conductive materials of the compartments.

In addition to being able to manage the problems of changing the power supply cable in case of infection from the percutaneous passage, such an embodiment of the connection system having an emergency power cable 6 positioned in situ further allows being able to quickly substitute a second power supply source for main power supply source 3 in case this source fails, or, for example, when main power supply cable 4 is damaged and can no longer supply electrical implanted medical device 2 with power.

As has already been mentioned, the electrical connection system proposed can be adapted to any type of implanted medical device preferably requiring a continuous power supply.

The electrical connection system proposed is especially suited to power supply for electrical medical devices serving to ensure the functioning of a failed organ, as is the case, for example, of the heart assist pump presented.

The electrical connection system proposed can also be used for other types of electrical implanted medical devices, such as, for example, devices intended to deliver medicinal substances directly inside the human body in a controlled manner.

This particular electrical connection system can also be used in order to electrically supply an implanted power generation device, such a power generation device being generally connected to several other implanted medical devices inside the patient's body.

Moreover, the electrical connection system proposed may be used to electrically connect any type of internal electrical device, i.e., implanted in the patient, to any type of external electrical device, including devices for collecting data measured inside the patient's body.

Electrical connection device 1 proposed comprises special electrical interconnection means 8 that allow connecting the electrical wires of main cable 4 to the electrical wires of the same phase of electrical implanted medical device 2 on one side, and to connect the electrical wires of a possible emergency power supply cable to the electrical wires of the same phase of electrical implanted medical device 2 on the other side. These interconnection means 8 can have a more or less complex structure.

According to the simplest form, the different connectors are connected by soldered wiring. According to a more complex embodiment, the interconnection means are created by means of a printed circuit that associates the connectors together so as to connect the electrical wires of the same phase according to a particular diagram, defined according to the needs identified.

According to one particular embodiment, interconnection means 8 can be activated via a selector that allows changing the electrical connections, for example to connect either main power supply cable 4 or emergency power supply cable 6 to electrical implanted medical device 2. In this case, a diode, for example, can indicate what electrical port is operational.

Electrical connection device 1 used in the electrical connection system proposed at the end of main power supply cable 4 can have different forms as long as electrical connection device 1 is adapted for implantation within the human body, and that it allows reliable electrical connection between various electrical wires coming from various devices or cables while offering removable connection of these different electrical wires.

In fact, for the electrical connection system presented above, it is vital to be able to have a connection device 1 that allows removable and reliable connection of main power supply cable 4, as well as removable, and as reliable as possible, connection of a possible secondary power supply cable 6, called emergency cable or backup cable.

Figure 2:
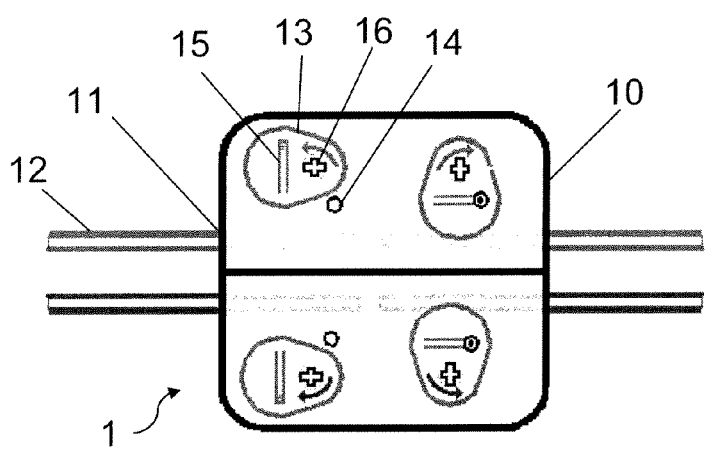
FIG. 2 is a schematic representation of an embodiment of the electrical connection device presented.

According to one particular embodiment, such as illustrated in FIG. 2, an electrical connection device 1 is proposed in the form of a housing 10 that comprises a certain number of internal cavities inside which it is possible to insert electrical wires 12 by means of openings 11 arranged at the surface of housing 10. Furthermore, electrical connection device 1 has interconnection means (not shown) that are designed to establish a specific electrical connection between the various electrical wires 12 inserted into electrical connection device 1, so as, in particular, to connect electrical wires 12 of the same phase provided for a power supply.

Note that housing 10 can have any shape, for example rectangular or oval. Moreover, the housing is preferably designed in a biocompatible material, as is any element making it up that could come into contact with the interior of the patient's body.

As mentioned above, it is necessary for electrical connection device 1 presented to be designed for a removable connection of electrical wires 12, while guaranteeing that electrical wire 12 is reliably held in position in the corresponding cavity when one does not wish electrical cable 12 to be disconnected from electrical connection device 1.

For this purpose, housing 10 integrates position maintenance means 13, preferably at each opening, so as to hold electrical wire 12 inserted through corresponding opening 11 in position. More precisely, the position maintenance means proposed comprises a cam 13 mounted rotatably in housing 10 so as to compress electrical wire 12 against the inner walls of the cavity when this wire is inserted through corresponding opening 11.

Cam 13, mounted rotatably in housing 10, therefore has a compression portion that can compress electrical wire 12 against the inner walls of the corresponding cavity when cam 13 is in a particular position, and a surface called neutral, which does not exert any pressure on electrical wire 12 when it is facing this surface.

Preferably, cam 13 is mounted rotatably in housing 10 so that rotation of cam 13 in a direction tending to insert electrical wire 12 inside the cavity brings the compression surface of the cam opposite said electrical wire 12 so as to compress it against the inner wall of the corresponding cavity.

Thus, when cam 13 is activated rotatably so as to come to compress the corresponding electrical wire, the rotation movement of cam 13 tends to insert the wire into housing 10 which is preferable for the reliability of the electrical connection within electrical connection device 1.

Preferably, the compression surface of cam 13 is adapted so as to mechanically engage electrical wire 12 designed to be compressed. Thus, the compression portion of cam 13 can, for example, be serrated or toothed, and/or rough, so that the compression surface can come to be engaged inside the sheath provided around electrical wire 12. Such a serrated or toothed compression surface of cam 13 allows not only a better engagement of electrical wire 12 in the cavity of housing 10, but also allows electrical wires with slightly different dimensions to be held in position 13. In fact, these diameter differences can be compensated for by the depth of insertion of the notches or teeth inside the sheath surrounding electrical wire 12.

According to a preferred embodiment, the position maintenance means further has a locking means (14, 15) designed to lock cam 13 when it is in the position of compressing electrical wire 12. This locking means (14, 15) therefore prevents electrical wire 12 from being removed from housing 10 unintentionally.

Such a locking means (14, 15) further comprises a locking component 14, slidably mounted, for example, inside housing 10, and being designed to cooperate with a complementary rail 15 provided in cam 13 for position maintenance. When cam 13 is turned so that the compression portion comes to compress electrical wire 12 against the inner wall of the cavity, locking component 14 comes to be inserted inside complementary rail 15 provided in cam 13. Locking component 14 slides inside complementary rail 15 provided in cam 13 until it comes to stop against the closed end of complementary rail 15 where a mechanism to lock locking component 14 in complementary rail 15 is provided. This mechanism can be, for example, a spring mechanism arranged to be automatically activated when locking component 14 is placed in a specific position inside complementary rail 15, for example stopped against the closed end of said complementary rail 15.

Thus, when cam 13 is in a position to compress electrical wire 12 against the inner walls of the cavity, this cam 13 is held locked in position by locking means (14, 15) described. This prevents electrical wire 12 from being withdrawn from connection device 1, which guarantees a reliable electrical connection between the various electrical wires 12. If it proves necessary to remove said electrical wire 12, it is sufficient to deactivate locking means (14, 15), for example by triggering the spring mechanism, if applicable.

Furthermore, electrical connection device 1 can be adjusted so that inserting electrical wires 12 into housing 10 is done in a sealed manner, i.e., the inside of the cavities created in housing 10 are insulated from the external environment of housing 10 when electrical wires 12 are in position, connected into said electrical connection device 1. To this end, it is preferable to create the seal mentioned at each of openings 11 created in housing 10.

Housing 10 can, for example, have a recess 111 at the peripheries of openings 11, said recess being designed to cooperate with a protrusion 121 provided on electrical wire 12 so that the cooperation between protrusion 121 and recess 111 forms a gasket between the inside of the cavity and the outside of housing 10 when electrical wire 12 is in position connected to the inside of the cavity.

Figure 3:
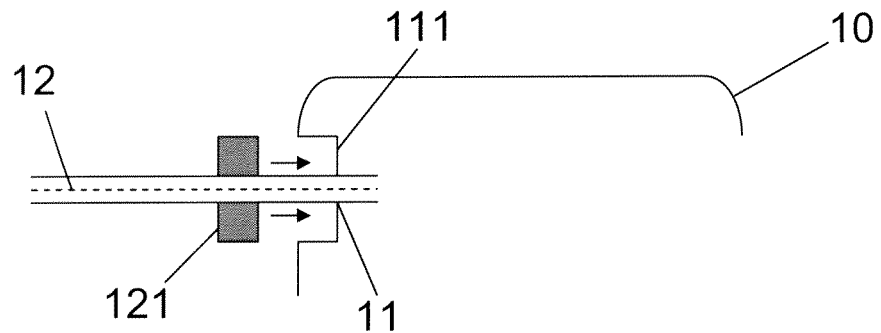
FIGS. 3 to 5 are schematic representations of the various embodiments of the sealing means for the electrical connection device of FIG. 2.
Figure 4:
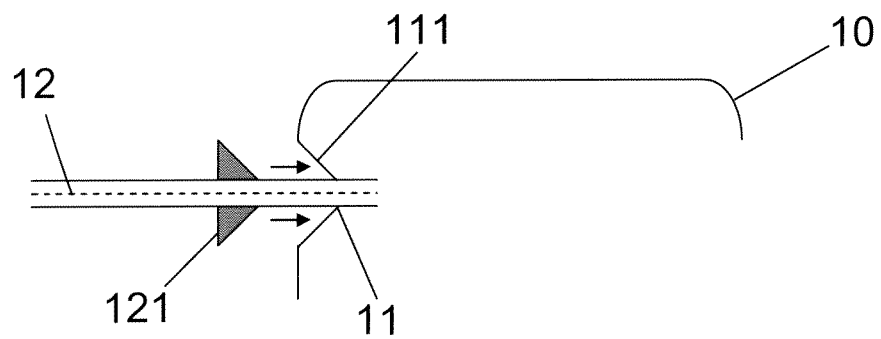
Figure 5:
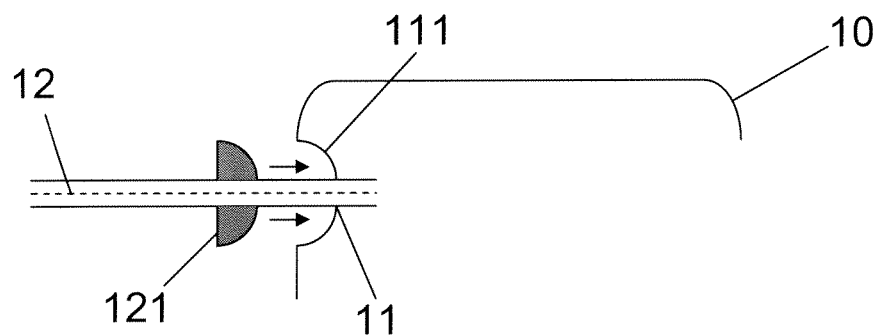

FIGS. 3, 4 and 5 illustrate particular embodiments of such a sealing arrangement by the cooperation of a recess 111 created in opening 11 of housing 10 with a protrusion 121 provided on electrical wire 12 intended to be inserted into said opening 11.

As illustrated in FIG. 3, recess 111 can have a cylindrical shape, protrusion 121 provided around electrical wire 12 then further having a cylindrical shape around the wire, complementary to cylindrical recess 111 created at the periphery of opening 11 of the housing.

According to another embodiment such as illustrated in FIG. 4, recess 111 created at opening 11 has a truncated shape designed to cooperate with a protrusion 121 having a ring shape that is also truncated surrounding wire 12.

A recess 111 can further be provided at opening 11 having a hemispherical shape to cooperate with a protrusion 121 created around electrical wire 12 and further having a hemispherical shape designed to cooperate with the hemispherical shape of recess 111.

Note that these last two embodiments are particularly effective to guarantee a certain seal between the inside of the cavity and the outside of housing 10 since the seal will be ensured even if there are imperfections when recess 111 is formed in the housing and/or protrusion 121 is formed on electrical wire 12.

An embodiment can further be considered in which the surface of housing 10 at opening 11 does not have any recess, in which case the seal between the inside of the cavity and the outside of housing 10 is ensured by protrusion 121 alone provided on wire 12 that rests against opening 11 and thus guarantees a certain seal. In this case, protrusion 121 can also have any shape whatever, preferably hemispherical, truncated, or even cylindrical.

Protrusion 121 provided on electrical wire 12 can be directly formed in the insulating sheath surrounding said electrical wire 12. According to a preferred embodiment, protrusion 121 provided to surround electrical wire 12 is formed in a sleeve that is designed to surround the insulating sheath of electrical wire 12 so that it is possible to position said protrusion 121 anywhere with regard to the end of electrical 12 that one wishes to connect to connection device 1. This is even more advantageous in that the position of protrusion 121 with respect to opening 11 is critical for the seal between the inside of the cavity and the outside of housing 10 to be as effective as possible. Even more preferably, cam 13, designed to hold wire 12 in position inside the cavity, is designed to cooperate with the sleeve bearing protrusion 121 around wire 12 so that cam 13 can hold in position not only electrical wire 12, but also protrusion 121 corresponding to it.

Furthermore, cam 13 has actuator means 16 that bring said cam 13 into the desired position, to hold electrical wire 12 fixed inside housing 10, for example, or to release this electrical wire 12. These actuator means 16 can have the shape of a specific notch, for example, into which it is possible to slide a tool from the outside of housing 10, such as, for example, a screwdriver, so that cam 13 can be rotated inside housing 10 mechanically, by a practitioner, which guarantees an even better reliability of electrical connection device 1 presented.

Although electrical connection device 1 has been presented in reference to the electrical connection system described above, its use is obviously not limited to the electrical connection system described. In particular, such an electrical connection device 1 can be used to connect together electrical medical devices implanted inside the patient's body, or even to enable electrical connection between an implanted power source and one or more electrical implanted medical devices, etc.

Moreover, electrical connection device 1 presented has been described in reference to a single cavity and a single opening provided for the connection of a single electrical wire. It goes without saying that the corresponding technical teaching can be adapted to form an electrical connection device 1 with several cavities, several openings and several position maintenance means for wires designed to be inserted into each opening, the interconnection means provided inside electrical connection device 1 being adjusted according to the needs of the electrical connection that one wishes to create by means of electrical connection device 1 presented.

Likewise, the electrical connection system has been presented in relation to the single issue of power supply for an electrical implanted medical device. However, it could be adapted for other purposes, for example to guarantee continuous transmission of data received by the implanted medical device or data controlling this implanted medical device. Preferably, the electrical connection system presented is used to ensure continuous power supply, as well as to permit reliable transmission of particular data, which simply requires adjusting the number of electrical wires integrated into the various cables, and the number of connectors of the connection device.

The reader will understand that numerous modifications can be introduced without materially exceeding the scope of the novel teachings and advantages described here. Consequently, all modifications of this type are intended to be incorporated in the scope of the invention.

The invention claimed is:

1. An electrical connection system to electrically connect an internal electrical device (2) designed to be positioned inside an animal's body with an external electrical device (3) designed to be positioned outside the animal's body, said system comprising a cable (4) designed to be positioned at least partially inside the animal's body and enclosing at least one electrical wire, said cable (4) having at a first end a first connection means (5) to connect said at least one electrical wire with the external electrical device (3), wherein the cable (4) further has at a second end a second connection means (1) designed to be placed inside the animal's body, the second connection means (1) having connectors configured to provide a removable electrical connection between said at least one electrical wire of the cable (4) and the internal electrical device (2), the second connection means (1) further having additional connectors configured to provide a removable electrical connection between at least one electrical wire external to said cable (4) and the internal electrical device (2).

2. The system of claim 1, further including a second cable (6) designed to be positioned at least partially inside the animal's body and enclosing at least one electric wire, said second cable (6) having at one end a third connection means (7) to connect said at least one electrical wire of the second cable (6) with an external electrical device, said at least one electrical wire of the second cable (6) being further connected to at least one of the additional connectors of second connection means (1), in order to connect the second cable (6) to internal electrical device (2).

3. The system of claim 2, wherein third connection means (7) of the second cable (6) is a subcutaneous electrical connector.

4. The system of claim 2, wherein third connection means (7) of the second cable (6) is an electrical connector n the form of a percutaneous socket.

5. The system of claim 1, wherein the first connection means (5) of the first cable (4) is an electrical connector in the form of a percutaneous socket.

6. The system of claim 1, wherein the connectors of the second connection means (1) have components (13) for compressing electrical wires, said compression components (13) having the form of rotatably-mounted cams configured to engage against said electrical wires.

7. The system of claim 6, wherein the connectors of second connection means (1) further comprise locking components (14, 15) configured to lock the rotation of compression components (13) in order to hold said compression components in position.

8. The system of claim 1, wherein the second connection means (1) configured to activate at least one of a) the electrical connection between said at least one electrical cable (4) and the internal electrical device (2), and b) the electrical connection between said at least one electrical wire external to said cable (4) and the internal electrical device (2).

9. A heart assist assembly comprising:
an internal electrical device (2) in the form of a heart assist pump intended to be implanted in an animal for replacing all or part of the animal's heart;
an electrical connection system to electrically connect the heart assist pump with an external electrical device (3) designed to be positioned outside the animal's body, said system comprising a cable (4) designed to be positioned at least partially inside the animal's body and enclosing at least one electrical wire,
said cable (4) having at a first end a first connection means (5) to connect said at least one electrical wire with the external electrical device (3),
wherein the cable (4) further has at a second end a second connection means (1) designed to be placed inside the animal's body, the second connection means (1) having connectors configured to provide a removable electrical connection between said at least one electrical wire of cable (4) and the heart assist pump, the second connection means (1) further having additional connectors configured to provide a removable electrical connection between at least one electrical wire external to said cable (4) and the heart assist pump.

10. An assembly for delivering a therapeutic substance inside an animal's body comprising:

an internal electrical device (2) in the form of a device for releasing a therapeutic substance designed to be implanted in an animal to allow delivering said therapeutic substance into specific areas for treating the animal;
an electrical connection system to electrically connect the device for releasing a therapeutic substance with an external electrical device (3) designed to be positioned outside the animal's body, said system comprising a cable (4) designed to be positioned at least partially inside the animal's body and enclosing at least one electrical wire,
said cable (4) having at a first end a first connection means (5) to connect said at least one electrical wire with the external electrical device (3),
wherein the cable (4) further has at a second end a second connection means (1) designed to be placed inside the animal's body, the second connection means (1) having connectors configured to provide a removable electrical connection between said at least one electrical wire of cable (4) and the device for releasing a therapeutic substance, the second connection means (1) further having additional connectors configured to provide a removable electrical connection between at least one electrical wire external to said cable (4) and the device for releasing a therapeutic substance.

11. A power generation assembly comprising:
an internal electrical device (2) containing an internal power supply device designed to be implanted in an animal and having means for being electrically connected to at least one medical device designed to be implanted in said animal;
an electrical connection system to electrically connect the internal power supply device with an external electrical device (3) designed to be positioned outside the animal's body, said system comprising a cable (4) designed to be positioned at least partially inside the animal's body and enclosing at least one electrical wire,
said cable (4) having at a first end a first connection means (5) to connect said at least one electrical wire with the external electrical device (3),
wherein the cable (4) further has at a second end a second connection means (1) designed to be placed inside the animal's body, the second connection means (1) having connectors configured to provide a removable electrical connection between said at least one electrical wire of cable (4) and the internal power supply device, the second connection means (1) further having additional connectors configured to provide a removable electrical connection between at least one electrical wire external to said cable (4) and the internal power supply device.

* * * * *

UNITED STATES PATENT AND TRADEMARK OFFICE
CERTIFICATE OF CORRECTION

| | | |
|---|---|---|
| PATENT NO. | : 8,545,261 B2 | Page 1 of 1 |
| APPLICATION NO. | : 13/262917 | |
| DATED | : October 1, 2013 | |
| INVENTOR(S) | : Pierre-Yves Litzler and Pierre Sabin | |

It is certified that error appears in the above-identified patent and that said Letters Patent is hereby corrected as shown below:

On the Title Page, in Item [54] and in the Specifications, at Column 1, Line 2, in the title, please delete "ELECTRICAL IMPLANTED" and insert --ELECTRICAL POWER SUPPLY DEVICE AND AN IMPLANTED--.

In the Claims, Column 11, Claim 4, line 8, please delete "n" and insert --in--.

Signed and Sealed this
Fourth Day of February, 2014

Michelle K. Lee
*Deputy Director of the United States Patent and Trademark Office*